(12) United States Patent
Cambrea et al.

(10) Patent No.: US 8,574,658 B1
(45) Date of Patent: Nov. 5, 2013

(54) FUMELESS LATENT FINGERPRINT DETECTION

(75) Inventors: Lee R. Cambrea, Ridgecrest, CA (US); Benjamin G. Harvey, Ridgecrest, CA (US)

(73) Assignee: The United States of America as Represented by the Secretary of the Navy, Washington, DC (US)

(*) Notice: Subject to any disclaimer, the term of this patent is extended or adjusted under 35 U.S.C. 154(b) by 192 days.

(21) Appl. No.: 13/035,590

(22) Filed: Feb. 25, 2011

(51) Int. Cl.
*A61B 5/103* (2006.01)
*A61B 5/117* (2006.01)

(52) U.S. Cl.
USPC .......................................................... 427/1

(58) Field of Classification Search
USPC .......................................................... 427/1
See application file for complete search history.

(56) References Cited

U.S. PATENT DOCUMENTS

| | | | | |
|---|---|---|---|---|
| 6,306,662 B1* | 10/2001 | Menzel | ......................... | 436/172 |
| 8,026,328 B2* | 9/2011 | Rowell | ............................ | 528/10 |
| 2011/0033607 A1* | 2/2011 | Pitts et al. | ........................ | 427/1 |

OTHER PUBLICATIONS

Menzel et al. Functionalized Europium Oxide Nanoparticles for Fingerprint Detection: A Preliminary Study, 2005, Journal of Forensic Identificaiton, 55 (2) pp. 189-195.*
Gordon, W.O.; Carter, J.A.; Tissue, B.M. J. Luminescence 2004, 108, 339-342.
Feng, J.; Shan, G.; Maquieira, A.; Koivunen, M.E.; Guo, B.; Hammock, B.D.; Kennedy, I.M. Anal. Chem. 2003, 75, 5282-5286.
Bazzi, R.; Glores-Gonzalez, M.A.; Louis, C.; Lebbou, K.; Dujardin, C.; Brenier, A.; Zhang, W.; Tillement, O.; Bernstein, E.; Perriat, P. J. Luminescence 2003, 102-103, 445-450.
Cheng, K.H.; Aijmo, J.; Ma, L.; Yao, M.; Zhang, X.; Como, J.; Hope-Weeks, L. J.; Huang, J.; Chen, W. J. Phys. Chem. C 2008, 112, 17931-17939.
Cheng, K.H.; Ajimo, J.; Wei, C. J. Nanoscience Nanotech 2008, 8, 1170-1173; Jurnal Teknologi, 36(C) Jun. 2002: 83-74.

\* cited by examiner

*Primary Examiner* — Kelly M Gambetta
(74) *Attorney, Agent, or Firm* — Charlene A. Haley

(57) ABSTRACT

A fumeless latent fingerprint detection system using fluorescent particles.

25 Claims, 4 Drawing Sheets

FUMELESS LATENT FINGERPRINT DETECTION

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to a method for fumeless latent fingerprint detection, and more specifically, the use of functionalized fingerprint powders that are made to specifically bind fingerprint residues.

Figure 1:
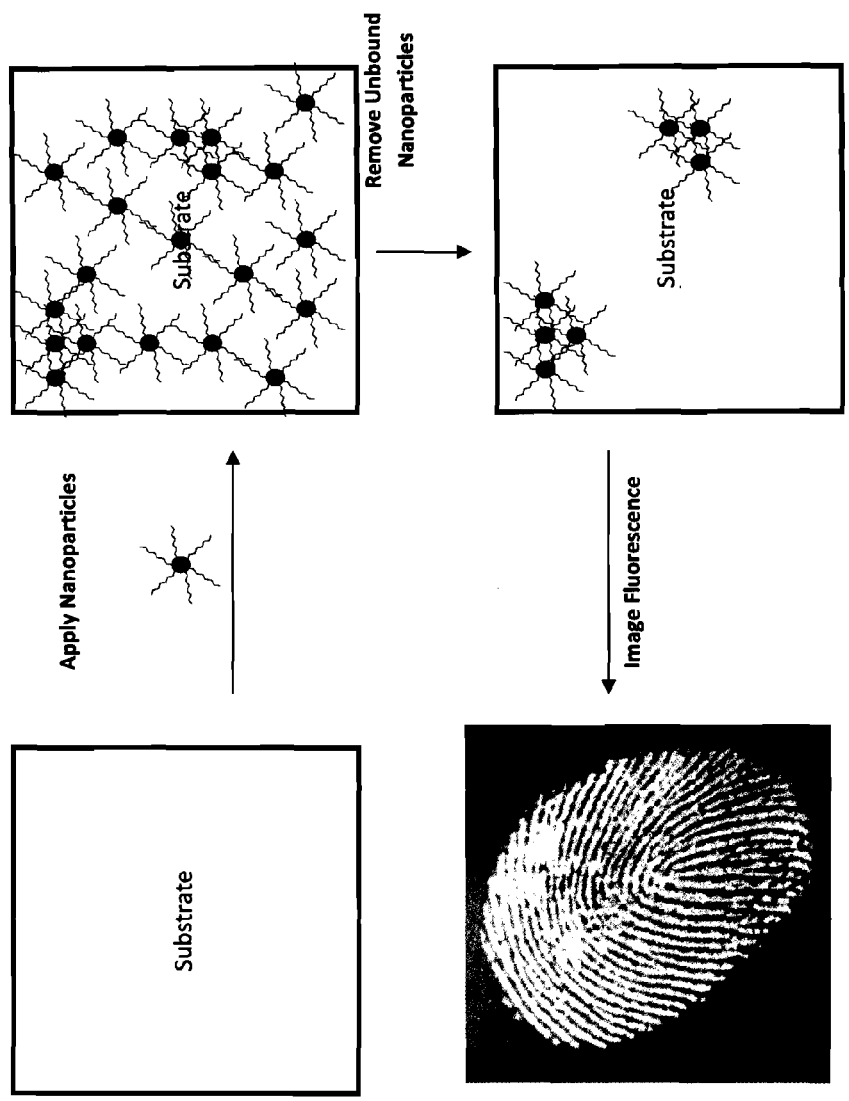
FIG. 1 is a an embodiment of the invention of the automated detection method which will spray an aerosol, or dust a powder, including fluorescent nanoparticles onto an item, remove unbound nanoparticles, and then capture the fluorescent, digital image of the latent fingerprints (positive image).

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to fumeless latent fingerprint detection.

The development of latent fingerprints is a time consuming process. Older techniques are based on the iodine/silver transfer method. This method involves a 5 step process: fuming iodine with a heat gun, directing fumes toward the location of the prints, placing a sheet of silver on the prints, removing the silver plate, and exposing the plate to a bright light source to expose the prints. Newer techniques use fuming superglue (cyanoacrylate) prior to manually dusting with either black, magnetic, or fluorescent powders.

Embodiments of the invention relate to a method for latent fingerprint detection including, providing at least one functionalized fluorescent particle capable of binding to at least one print residue, applying the particles to a surface/substrate and determining whether the surface/substrate includes the residue, substantially removing unbound and excess particles from the surface/substrate, and detecting remaining bound particles through their fluorescence.

Another aspect of the invention relates to a fumeless detection system for acquiring latent prints including, at least one functionalized fluorescent particle binding to at least one print residue, a surface/substrate suspected of having the residue thereon and applying the particles to the surface/substrate, where the unbound and excess particles are substantially removed from the surface/substrate, and where bound particles remaining are detected by fluorescence.

In embodiments, the particles can be many types and sizes of particles including, but not limited to, nanoparticles, lanthanide doped particles, micron sized particles, non-fluorescent particles, and any combination thereof. In other embodiments, the particles can be nanoparticles composed of a lanthanide oxide. In other embodiments, particles can be composed of various support materials including alumina, silica, or various polymers. These particles are chemically bound to appropriate lanthanide based molecules through the use of chelating agents and are further functionalized in the manner described previously. The method of functionalization described above can also be applied to larger micron sized particles or non-fluorescent particles allowing for other methods of detection including white light visualization.

In embodiments, the residue may come from prints from either humans or animals. These print residues may come from fingerprints, nose prints, foot prints, or any combination of prints or prints that produce a specific detectable residue. In embodiments, the residues are selected from the group consisting of triglycerides, wax esters, squalene, water, salts, proteins, and any combination thereof.

In embodiments, the method including "detecting remaining bound particles" utilizes optical filters and a broadband UV source to detect fluorescence. In embodiments, the method further includes imaging and processing the detected bound particles. In embodiments, the step of "applying the particles" includes, but is not limited to, techniques utilizing hydrophobic and/or specific covalent or ionic interactions. In embodiments, the particles are in the form of an aerosol or powder and are sprayed or dusted onto a surface/substrate.

Lanthanide oxides have a broad excitation and narrow emission profile for fluorescence. Excitation window is in the ultraviolet (10-400 nm) and emission is in the visible (400 nm-800 nm. Fluorescent nanoparticles primarily based on lanthanide oxides have been studied as versatile labeling and imaging materials due to their long fluorescence lifetimes, high quantum yields, and sharp emission spectra profiles. (Gordon, W. O.; Carter, J. A.; Tissue, B. M. J. Luminescence 2004, 108, 339-342) Additionally, the ability to functionalize these particles with a variety of chemical moieties allows for exquisite control of solubility, aggregation, and surface chemistry. (Feng, J.; Shan, G.; Maquieira, A.; Koivunen, M. E.; Guo, B.; Hammock, B. D.; Kennedy, I. M. Anal. Chem. 2003, 75, 5282-5286; Bazzi, R.; Glores-Gonzalez, M. A.; Louis, C.; Lebbou, K.; Dujardin, C.; Brenier, A.; Zhang, W.; Tillement, O.; Bernstein, E.; Perriat, P. J. Luminescence 2003, 102-103, 445-450) Given their unique set of properties, lanthanide oxide based nanoparticles have previously been investigated as fluorescent agents to image fingerprints. (Cheng, K. H.; Aijmo, J.; Ma, L.; Yao, M.; Zhang, X.; Como, J.; Hope-Weeks, L. J.; Huang, J.; Chen, W. J. Phys. Chem. C 2008, 112, 17931-17939; Cheng, K. H.; Ajimo, J.; Wei, C. J. Nanoscience Nanotech 2008, 8, 1170-1173; Jurnal Teknologi, 36(C) June 2002: 83-74)

A rapid, high throughput process for imaging latent fingerprints to aid in the identification of suspects is required.

Instead of taking evidence back to a lab for complete fingerprint analysis, embodiments of this invention allow for the real time development and digital storage of fingerprints, in the field, on a variety of substrates. The ability to quickly identify fingerprints on evidence in the field will increase the chances of matching latent prints to individuals in the area.

Automation of latent fingerprint detection and processing is hindered by the time consuming and labor intensive process of fuming prior to dusting with powders. After dusting, the prints are typically removed from the surface, sealed, and taken back to the lab for analysis. The fuming process and removal of the prints are often destructive to the evidence/substrate and are also time consuming steps toward identification. Embodiments of this invention allow for real time analysis of fingerprints in the field.

A new method of developing latent fingerprints without the need for fuming techniques has been discovered. Embodiments of this method include the use of lanthanide oxide nanoparticles functionalized to specifically bind to fingerprint residues and provide for fluorescence detection under broadband ultraviolet illumination. Lanthanide oxide nanoparticles have very narrow fluorescence emission bands allowing optical filters to be used to eliminate background fluorescence. By eliminating the need for a special fuming chamber or time consuming hand dusting steps, automation is easily achieved.

Specific binding of nanoparticles is accomplished through hydrophobic and/or specific ligand interactions (Van der Waals forces, covalent attachment, ionic attachment), completely eliminating the need for fuming. Lanthanide oxide nanoparticles are inherently fluorescent with broad excitation bands, narrow emission bands, and long fluorescent lifetimes. These qualities are in contrast to typically used fluorescent powders that have narrow excitation bands, broad emission bands, and short fluorescent lifetimes. Narrow excitation bands force the use of a specific illumination source e.g. a narrow band UV light or occasionally a laser source. These sources can be expensive and only work for a single fluorophore. Broad emission bands can lead to fluorescence resonance energy transfer where the fluorescence energy from the powder is transferred to nearby materials making the background signal amplify and the latent print signature diminish. Short fluorescent lifetimes cause difficulties in distinguishing between the natural fluorescence of nearby materials and the fluorescently labeled print. The use of lanthanide oxide nanoparticles eliminates the need for fluorescent powder dusting and also solves the above mentioned problems. This latent print development method lends itself to easier automation than current techniques.

FIG. 1 shows an embodiment of the invention of the automated detection method in which fluorescent nanoparticles are sprayed as an aerosol or dusted as a powder onto a substrate, unbound nanoparticles are removed, and then the fluorescent, digital image of the latent fingerprints (positive image) is captured.

Extensive laboratory testing was performed and field testing is in progress to determine the binding ability of various nanoparticles and any associated limitations.

Figure 2:
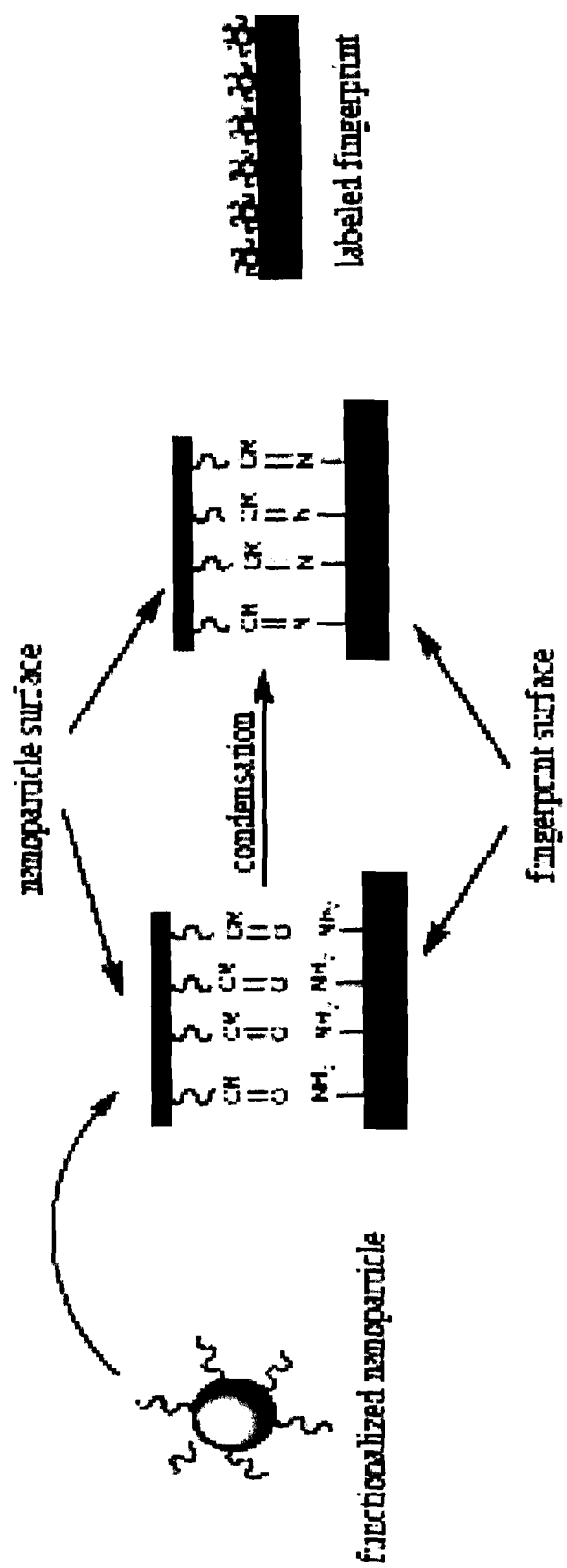
FIG. 2 is a schematic illustration depicting the reaction of pendant carbonyl functionalized nanoparticles with fingerprint residues, according to embodiments of the invention.

In one of the embodiments of the process, the initial step is the synthesis of functionalized lanthanide oxide nanoparticles. To increase selectivity, the particles can be functionalized with a variety of reactive groups tailored to covalently bond or interact with fingerprint residues. The functionalities range from simple long chain alkanes for hydrophobic interactions to pendant carbonyl groups that can react with amines included in the residue (as in the ninhydrin reaction), FIG. 2. The chain length and hydrophobicity of the functional group dictates the degree of solubility/reactivity of the particles. In the step of applying the particles, techniques utilizing hydrophobic (e.g. long chain alkanes including palmitic acid or trioctylphosphine oxide ligands) interactions can be used.

Embodiments for a method of developing latent fingerprints without the need for fuming techniques include, but are not limited to: functionalized lanthanide oxide nanoparticles are applied to the substrate and bind to the fingerprint residue, excess and unbound nanoparticles are removed, the inherent fluorescence of the nanoparticles is used for detection, imaging and processing of the latent prints is achieved using a camera system operated by a graphical user interface on a laptop computer. Lanthanide oxide nanoparticle are ideal for this application due to their inherent fluorescence characteristics, specific binding, and small size (shown in Table 1).

TABLE 1

|  | Nanoparticles | Organic Powders |
| --- | --- | --- |
| Excitation | Broad | Narrow |
| Emission | Narrow | Broad |
| Interaction w/Print | Specific Covalent | Non-Specific |
| Sample Preparation | None | Fuming Cyanoacrylate |
| Particle Size | Nanometer | Micron |

Figure 3:
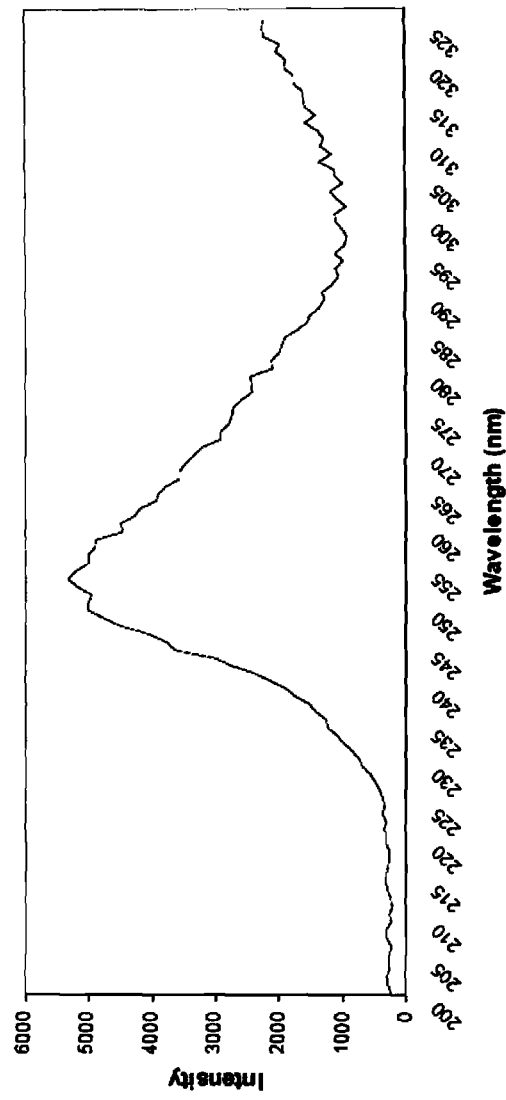
FIG. 3 is an excitation spectrum of a mixed lanthanide oxide showing that the width of the excitation peak allows for a broadband excitation source (lamp) which translates into rapid imaging of large areas, according to embodiments of the invention.

FIG. 3 is a graph illustrating a mixed lanthanide excitation spectrum. The width of the excitation peak allows for a broadband excitation source (lamp) which translates into the ability to quickly image large areas.

Figure 4:
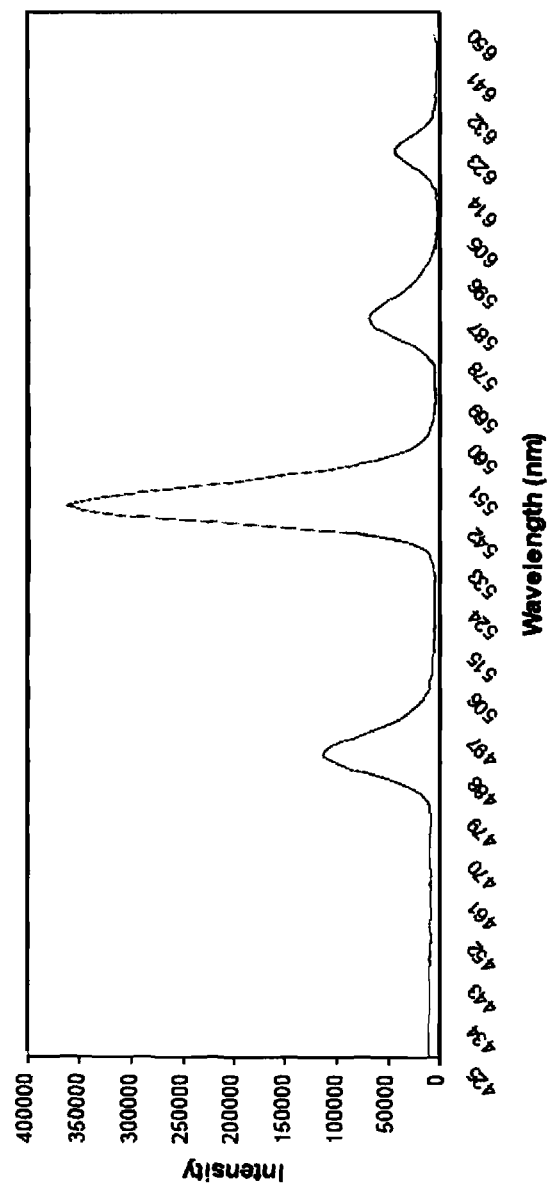
FIG. 4 is a mixed lanthanide oxide emission spectrum showing sharp, long-lived emission that allows for selective target identification with elimination of background through appropriate filters and further shows that mixed nanoparticle systems can provide unique emissive patterns to improve selectivity, according to embodiments of the invention.

FIG. 4 is a graph illustrating a mixed lanthanide emission spectrum. The observed sharp, long-lived emission peaks allow for selective target identification with elimination of background through use of appropriate filters. This figure also shows that mixed nanoparticle systems can provide unique emissive patterns to further improve selectivity.

Luminescent NP Synthesis

Nanoparticles can be synthesized (See the equation below) under basic conditions to form stable, colorless, aqueous suspensions.

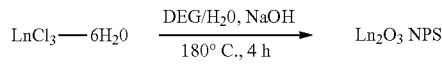

*Ln = Eu, Tb, and/or Nd

Ionic Liquid Nanoparticles

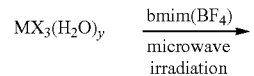

M = Eu, Nd, Er, Ce
X = Cl$^-$, NO$_3^-$

bmim(BF$_4$) = 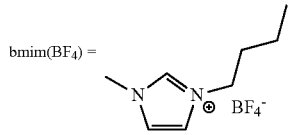

The above shows the synthesis of luminescent nanoparticles by decomposition of lanthanide salts with microwave irradiation in ionic liquids. This method allows for rapid synthesis (on the order of several minutes) and is economical for the production of lanthanide oxide nanoparticles.

The equation below shows the synthesis of mixed lanthanide NPs. This method allows for the synthesis of nanoparticles with both magnetic and luminescent properties.

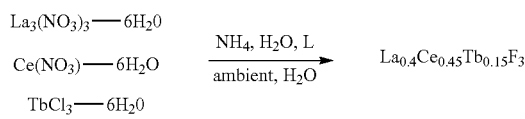

PEG Ligand, L = $OHCO(CH_2CH_2O)_3OCOH$

Lipophilic, $Eu_2O_3$ Nanoparticles

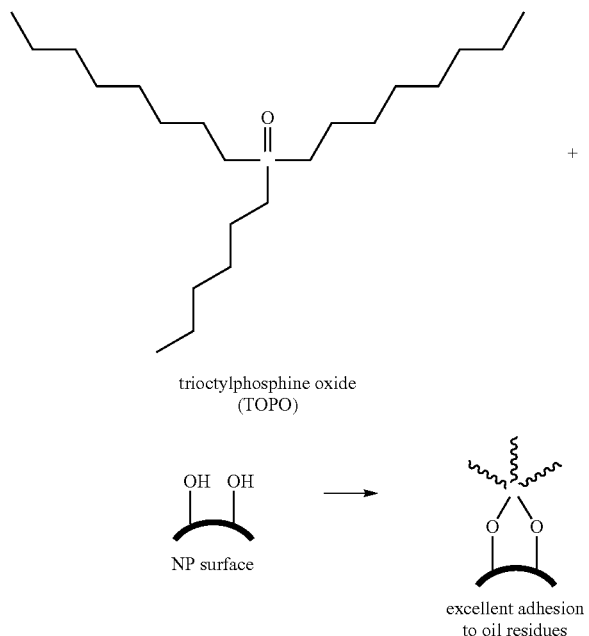

The above scheme illustrates the reaction of lipophilic, fluorescent $Eu_2O_3$ nanoparticles that efficiently bind to fingerprint residues.

$Eu_2O_3$ NPs with Bifunctional Isocyanide Ligands

The scheme below shows an example method of the synthesis of isocyanide functionalized NPs. The isocyanide ligands bind in a manner similar to fuming superglue allowing for these particles to act as a solid-state, non-fuming alternative to cyanoacrylate based methods.

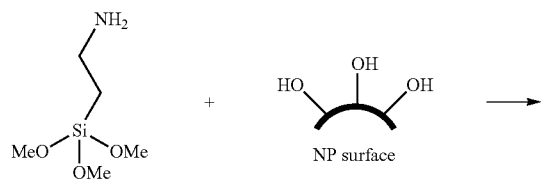

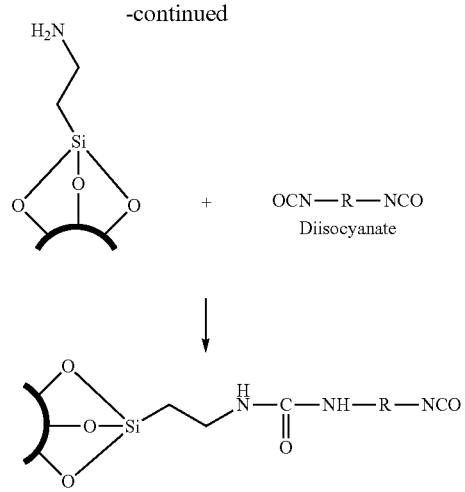

The scheme below shows the high-yield synthesis of magnetite NPs having nanoscale magnetic properties, and controllable solubility depending on ligand choice.

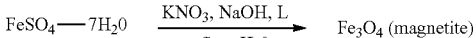

L= CTAB (cetyltrimethylammonium bromide) or other ligand

The nanoparticles with the most promising functionalities defined in the lab testing phase have undergone various laboratory tests to determine the effects of fingerprint age, substrate types, non-oily latent print binding, and non-specific binding (to the substrate). Fingerprint age studies have determined the ability of the nanoparticles to bind to latent fingerprints. The binding ability decreases with the age of the fingerprint due to the degradation of residue oils. However, due to the specific binding and high quantum yield of fluorescence (visible by the naked eye) detection can still be achieved for latent prints with placement ages beyond 30 days. A typical finger print has a ridge density of 11-12 ridges/25 mm$^2$: typical nanoparticles have diameters of approximately 10 nm indicating that a large number of nanoparticles are capable of binding, further increasing the probability that enough nanoparticles will be present for optical detection. Variations in substrate type can affect the ability of the NP to bind. Generally, more porous substrates absorb fingerprint residues leading to more difficult detection. An additional advantage of these NPs is their ability to stabilize latent fingerprints for travel or shipment. Latent prints are known to be rather delicate; however after dusting, latent prints have been exposed to air streams, high temperature, and physical shaking environments without damage.

Common Types of Fingerprints:
  Visible—Made in deposits of other materials.
  Imprint—Similar to visible only the negative impression.
  Latent—Not visible to the naked eye, difficult to find.

Non-specific binding causes an increase in background fluorescence thereby decreasing the clarity of fingerprint images. A number of strategies such as physical (gas stream, shaking), electrostatic, and magnetic separations have been evaluated. In the case of electrostatic separation, the high surface charge of the nanoparticles can be exploited, while for magnetic separation, magnetic core-shell particles can be synthesized and unbound particles separated with the aid of a magnet. The optimization of these methods leads to the above mentioned 3 step process (FIG. 1). Optimization of the nanoparticles and application protocols will be completed throughout this stage of full laboratory testing.

The newly developed approach uses lanthanide oxide nanoparticles functionalized to specifically bind to fingerprint residue oils consisting of triglycerides, wax esters, squalene, amino acids, urea, and salts. Once bound to the fingerprint residue, the inherent fluorescence of the nanoparticles is used for detection. This technique is unique in that the nanoparticles are synthesized to specifically bind to residue oils; additionally, detection is simplified compared to currently used organic fluorophore powders since the nanoparticles have a broad excitation and narrow emission profile. These fluorescent properties of the nanoparticles allow a broadband UV source to be used for illumination and optical filters to be used to selectively detect only the fluorescence from the nanoparticles: emission occurs in a several nanometer wavelength range.

The particles are synthesized from hydrated lanthanide salts of general formula $LnX_3\cdot yH_2O$, where Ln represents a lanthanide, i.e. La, Ce, Pr, Nd, Pm, Sm, Eu, Gd, Tb, Dy, Ho, Er, Tm, Yb, Lu, and X represents an anion, e.g. Cl—, Br—, I—, $NO_3$—, Cl— or $NO_3$—. Y is a non-integer or integer real number from 0 to 10, but typically from 2 to 6. The appropriate lanthanide salt is dissolved in an anhydrous alcoholic solvent, for example, methanol, ethanol, propanol, isopropanol or mixtures thereof in the presence of a dispersing agent, for example trioctylphosphine oxide, and a dilute solution of hydroxide is added until the solution is slightly basic. The precipitated particles are isolated by centrifugation, washed several times with fresh solvent and dried in vacuo. The particles can be further functionalized by treatment with 3-(triethoxysilyl) propyl amine at elevated temperature (60-80° C.) for 4-24 hrs. The functionalized particles are separated by filtration and are washed several times with diethyl ether and are then functionalized with rigid pendant isocyanate groups by reaction with aromatic diisocyanate groups in an organic solvent. Alternatively, commercial or lanthanide oxides or fluorides made by other methods can be directly functionalized by reaction with triethoxysilyl functionalized alkyl or aryl isocyanates. Mixed nanoparticle systems can also be made that utilizes several particle types with divergent functionalities (i.e. long chain hydrocarbon, isocyanate, and PEG ligands) to bind to different moieties in the residue. In embodiments of the invention, magnetite nanoparticles can be prepared either in situ or ex situ and act as seed particles for growth of lanthanide oxide nanoparticles. The resulting particles have both magnetic and luminescent properties. Nanoparticles can be applied via several pathways including aerosols, puffed powders, and liquid dispersions.

In summary, the automation of latent fingerprint detection is hampered by the complicated and time-consuming fuming process. A fumeless lanthanide oxide nanoparticle system was developed to eliminate this problem. Fluorescent nanoparticles were synthesized with specific binding interactions to fingerprint residue. The small size of the nanoparticles coupled with the specific binding allows for better detection of latent prints.

This invention has applications for latent fingerprint detection on a variety of surfaces including, but not limited to porous (e.g. documents) and non-porous (e.g. metals). This technology could be utilized by all forensics agencies that require latent fingerprint detection including: local, state and federal law enforcement/agencies, and military forensics units.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for latent print detection, comprising:
providing at least one type of fluorescent particle;
functionalizing said particles by covalently or ionically bonding a telechelic, multi-functional ligand to the surface that allows for covalent or ionic bonding directly to print residue;
applying said functionalized, dry particles to a surface/substrate and determining whether said surface/substrate includes said residue;
substantially removing unbound and excess said particles from said surface/substrate; and detecting remaining bound said particles through their fluorescence with a broadband UV source in real time.

2. The method according to claim 1, wherein said particles are polycrystalline or amorphous nanoparticles.

3. The method according to claim 1, wherein said prints are either human or animal.

4. The method according to claim 1, wherein said print is selected from the group consisting of fingerprint, nose print, and/or foot print.

5. The method according to claim 2, wherein said nanoparticles include a lanthanide oxide.

6. The method according to claim 1, wherein said particles comprises lanthanide coordination complexes or lanthanide oxide particles in a desired proportion.

7. The method according to claim 1, wherein said particles are micron sized particles.

8. The method according to claim 1, wherein said particles are non-fluorescent particles.

9. The method according to claim 1, wherein said residues are composed of molecules selected from the group consisting of triglycerides, wax esters, squalene, water, salts, proteins, and any combination thereof.

10. The method according to claim 1, wherein said particles have a broad excitation and narrow emission profile for fluorescence.

11. The method according to claim 1, wherein said detecting of remaining bound said panicles utilizes optical filters and a broadband UV source to detect fluorescence.

12. The method according to claim 1, further comprising imaging and processing said detected bound particles.

13. The method according to claim 1, wherein said particles are composed of various support materials including alumina, silica, various polymers, or any combination thereof.

14. The method according to claim 1, wherein said particles are in the form of an aerosol or powder and are sprayed or dusted onto said surface/substrate.

15. The method according to claim 1, wherein said ligands have a pendant isocyanate group, hydrophobic chain, polyol, or ionically charged group available for bonding interactions with the fingerprint residue.

16. The method according to claim 1, wherein said particles are magnetic and capable of forming ionic or covalent bonds directly with fingerprint residues.

17. A fumeless detection system for acquiring latent prints, comprising:

at least one type of fluorescent particles;

functionalizing said particles by covalently or ionically bonding a multifunctional telechelic ligand to the surface that allows for covalent or ionic bonding directly to print residue;

applying said dry particles to a surface/substrate, wherein said unbound and excess said particles are substantially removed from said surface/substrate; and wherein bound particles remaining are detected by fluorescence due to excitation from a broadband UV source in real time.

18. The system according to claim 17, wherein said particles are polycrystalline or amorphous nanoparticles.

19. The system according to claim 17, wherein said prints are either human or animal.

20. The system according to claim 17, wherein said print is selected from the group consisting of fingerprint, nose print, and/or foot print.

21. The system according to claim 18, wherein said nanoparticles include a lanthanide oxide.

22. The method according to claim 17, wherein said particles comprises lanthanide coordination complexes or lanthanide oxide particles in a desired proportion.

23. The system according to claim 17, wherein said particles are micron sized particles.

24. The system according to claim 17, wherein said particles are non-fluorescent particles.

25. The system according to claim 20, wherein said particles are magnetic and capable of forming ionic or covalent bonds directly with fingerprint residues.

* * * * *